United States Patent [19]

Qualeatti

[11] 4,338,221

[45] Jul. 6, 1982

[54] CATALYST FOR THE REDUCTION OF UNSATURATED ORGANIC ACIDS

[75] Inventor: Gail M. Qualeatti, Palatine, Ill.

[73] Assignee: UOP Inc., Des Plaines, Ill.

[21] Appl. No.: 233,416

[22] Filed: Feb. 11, 1981

[51] Int. Cl.³ .................. B01J 23/06; B01J 23/36; B01J 23/60; B01J 23/64
[52] U.S. Cl. ..................... 252/455 R; 252/457; 252/473; 252/475; 560/225; 568/885; 252/466 PT
[58] Field of Search ............ 252/455 R, 457, 466 PT, 252/473, 475; 560/225; 568/885

[56] References Cited

U.S. PATENT DOCUMENTS

| | | | |
|---|---|---|---|
| 2,646,394 | 7/1953 | Green et al. | 568/885 |
| 3,951,782 | 4/1976 | Buss | 252/441 X |
| 4,104,478 | 8/1978 | Trivedi | 568/885 |
| 4,231,897 | 11/1980 | Antos | 252/466 PT |

*Primary Examiner*—W. J. Shine
*Attorney, Agent, or Firm*—James R. Hoatson, Jr.; Raymond H. Nelson; William H. Page, II

[57] ABSTRACT

Unsaturated carboxylic acids may be subjected to a reduction process in which the resulting product retains the unsaturation of the starting acids by effecting the reaction in the presence of a catalyst comprising cadmium and rhenium composited on a solid support such as alumina. If so desired, the catalyst composite may also contain a noble metal of Group VIII of the Periodic Table.

8 Claims, No Drawings

CATALYST FOR THE REDUCTION OF UNSATURATED ORGANIC ACIDS

BACKGROUND OF THE INVENTION

It is known that unsaturated carboxylic acids may be reduced to the corresponding alcohol. However, the reducing catalysts which have heretofore been employed are not selective in the hydrogenation process, and thus the reductive process usually results in eliminating the retention of the unsaturation in the carbon chain. The compound which is obtained is therefore a saturated alcohol. This is true when utilizing catalysts such as a mixture of copper and chromium oxide, rhenium catalysts which may be used in either a supported or unsupported state or which may also contain a noble metal of Group VIII of the Periodic Table, such as platinum, palladium or ruthenium.

In many instances, it is desired to retain the unsaturation of the carbon chain when obtaining either alcohols or esters of the starting unsaturated acid. As will hereinafter be shown in greater detail, it has now been discovered that by utilizing a novel catalytic composition of matter, it is possible to effect a reductive reaction in which the double bonds present in the unsaturated carboxylic acid will be retained.

DETAILED DESCRIPTION OF THE INVENTION

This invention relates to a process for the reduction of unsaturated carboxylic acids. More specifically, the invention is concerned with a process for treating unsaturated carboxylic acids of the type hereinafter set forth in greater detail to effect a reduction of said acids utilizing a novel catalytic composite.

Unsaturated acid esters, especially those which possess a relatively long carbon atom chain, will find a wide variety of uses in the chemical field. The unsaturated acid esters, as exemplified by oleyl oleate, may be used as a substitute for sperm whale oil which is becoming increasingly difficult to obtain. Sperm whale oil is used as a high grade lubricating oil for light machinery such as watches, clocks and scientific instruments as well as in heat treating and rust proofing. In addition to use as a lubricant, the esters which are obtained according to the process of this invention may also be used in cosmetics such as perfumes, colognes, bath oils, soaps, powders, etc. This is especially true in the case of relatively long chain unsaturated esters.

In like manner, unsaturated alcohols are also useful in the chemical industry. For example, oleyl alcohol (octadecenol) may be used in chemical synthesis, as a petroleum additive, as a surface active agent, or in polymers. Likewise, behenyl alcohol may be used as a lubricant or in the production of synthetic fibers, while erucyl alcohol may also be used as a lubricant, surfactant or as an intermediate in the preparation of plastics, textiles and rubbers.

It is therefore an object of this invention to provide a catalyst for the reduction of unsaturated carboxylic acids.

A further object of this invention is to provide a novel catalytic composition of matter which may be utilized in a process for the reduction of an unsaturated carboxylic acid whereby the unsaturation which is present in the carbon atom chain will be retained.

In one aspect, an embodiment of this invention will be found in a catalyst composite for the reduction of an unsaturated acid comprising cadmium and rhenium composited on a solid support.

A specific embodiment of this invention is found in a catalytic composition for the reduction of an unsaturated acid comprising from about 1% to about 10% by weight of cadmium, from about 0.5% to about 5% by weight of rhenium, and from about 0.01% to about 2.5% by weight of platinum composited on gamma-alumina.

Other objects and embodiments may be found in the following further detailed description of the invention.

As hereinbefore set forth, the present invention is concerned with a novel reduction catalyst which will permit the reduction of an unsaturated carboxylic acid in the presence of hydrogen to form an ester or an alcohol without an appreciable effect on the unsaturation which is found in the carbon atom chain. The reduction process, utilizing these novel compositions of matter, is effected by treating an unsaturated carboxylic acid in the presence of the catalysts at conditions which will include a temperature in the range of from about 100° C. up to about 500° C. and superatmospheric pressures ranging from about 100 to about 5000 psig. The superatmospheric pressures may be afforded by hydrogen or, if so desired, the amount of hydrogen present may afford only a partial pressure, the remainder of the desired operating pressure being afforded by the presence of an inert gas such as nitrogen, helium, argon, etc. in the reaction vessel. The reduction process may be effected for a period of time which may range from about 0.5 up to about 10 hours or more in duration, the reaction time being determined by the unsaturated carboxylic acid undergoing reduction as well as the reaction temperature and amount of pressure which is employed during the reaction.

Examples of unsaturated carboxylic acids which may be employed as starting materials to form the desired unsaturated esters or alcohols will include those acids containing from 3 to about 22 carbon atoms, some specific examples of these acids being acrylic acid, the isomeric butenic acids such as crotonic acid, isocrotonic acid, vinyl acetic acid, methylacrylic acid, the isomeric pentenic acids such as tiglic acid, angelic acid, senecioic acid, the isomeric hexenic acids, heptenic acids, octenic acids, nonenic acids, decenic acids, undecenic acids, dodecenic acids, tridecenic acids, tetradecenic acids, pentadecenic acids, hexadecenic acids such as hypogeic acid, heptadecenic acids, octadecenic acids such as oleic acid, eladic acid, nonadecenic acid, eicosenic acids, erucic acid, brassidic acid, behenic acid, etc. It is to be understood that the aforementioned unsaturated carboxylic acids are only representative of the type of compounds which may be employed to form the desired esters, and that the present invention is not necessarily limited thereto.

The novel composition of matter of the present invention which is employed to effect the reduction of the aforementioned acids will comprise a catalyst composite comprising cadmium and rhenium composited on a solid support. In addition, if so desired, the catalyst composite may also contain a noble metal of Group VIII of the Periodic Table also composited on the solid support such as platinum, palladium, ruthenium, rhodium, etc. The cadmium will be present on the solid support, usually in the form of cadmium oxide, in an amount in the range of about 1% to about 10% by weight of the catalyst composite. Likewise, the rhenium which is present on the catalyst composite in any of its oxidation states, an oxidation state lower than +7 being preferred, is present in an amount in the range of from about 0.5% to about 5% by weight of the catalyst composite, while the nobel metal, if one is utilized to form the desired catalyst composite, will be present in zerovalent state in an amount in the range of from about 0.01% to about 2.5% by weight of the finished composite.

The aforementioned cadmium and rhenium, along with, if so desired, a noble metal of Group VIII of the Periodic Table are composited on the solid support which, in the preferred embodiment of the invention, comprises a relatively high surface area inorganic oxide. Examples of these inorganic oxides will include aluminas such as gamma-alumina, eta-alumina, theta-alumina, silica, or mixtures of inorganic oxides such as alumina-silica, silica-zirconia, silica-magnesia, alumina-silica-zirconium, etc.

The preparation of the novel reduction catalysts of the present invention may be effected in any suitable manner. An example of the type of preparation which may be used comprises steam impregnating the solid support such as gamma-alumina with an aqueous solution of a rhenium-containing composite such as ammonium perrhenate, perrhenic acid, etc. for a period of time which is sufficient to allow the deposition of the desired amount of rhenium on the solid support, that is, an amount sufficient so that the finished catalyst composite will contain from about 0.5 to about 5% of rhenium. After recovery of the impregnated solid support, the composite is then calcined at a temperature in the range of from about 250° to about 750° C. in an air atmosphere for a period of time which may range from about 0.5 up to about 4 hours in duration. The calcined composite is then subjected to a reducing treatment by heating the composite at a temperature within the range hereinbefore set forth in a hydrogen atmosphere. In the event that it is desired to have a noble metal of Group VIII of the Periodic Table also present in the catalyst composite, this metal is co-impregnated with the rhenium utilizing an aqueous solution of a noble metal-containing compound such as chloroplatinic acid, chloropalladic acid, ruthenium chloride, rhodium chloride, etc. Following the co-impregnation, the composite is then treated in a manner similar to that hereinbefore set forth, that is, it is calcined and reduced. As in the case of the rhenium, the co-impregnation with the noble metal is also effected by utilizing a sufficient amount of aqueous solution so that the noble metal will be present in the final catalyst composite in an amount in the range of from about 0.01 to about 2.5% by weight of the finished composite.

The thus formed composite containing rhenium and, if so desired, a noble metal, is thereafter steam impregnated with a solution of cadmium salt, said cadmium being present in an amount so that the finished catalyst will contain from about 1 to about 10% by weight of cadmium. Examples of cadmium salts which may be employed to effect the impregnation will preferably consist of organic salts of cadmium such as cadmium formate, cadmium acetate, cadmium propionate, etc., although it is also contemplated within the scope of this invention that some inorganic salts of cadmium, such as cadmium chloride, cadmium bromide, cadmium phosphate, etc. may also be employed, although not necessarily with equivalent results. In the preferred embodiment of the invention, the impregnation of the catalyst composite with cadmium is effected under a nitrogen blanket in order to provide an inert atmosphere for the aforesaid impregnation step. After allowing the impregnation with the cadmium salt to be effected for a predetermined period of time which may range from about 0.5 up to about 4 hours or more in duration, the resultant composite is then recovered and calcined under a nitrogen blanket at a temperature in the range of from about 250° to about 400° C. to form cadmium oxide. Upon completion of the calcination period, the resulting composite, which forms the novel reduction catalyst of the present invention, is recovered for utilization in a reduction process whereby an unsaturated acid may be reduced to an unsaturated ester or unsaturated alcohol.

It is also contemplated within the scope of this invention that the novel reduction catalyst may be prepared in a continuous manner of operation. When such a type of operation is employed, the solid support material comprising an inorganic oxide which may be of any desired shape, such as pellets, spheres, globules, rods, etc., is continuously passed through an aqueous solution of rhenium at a predetermined rate of speed in order that the predetermined amount of rhenium may be impregnated on the support. The support, after passage through the solution, is continuously withdrawn and passed to a calcination zone wherein it is treated at an elevated temperature, in the presence of air, within the range hereinbefore set forth. After completion of the calcination period, the rhenium impregnated material is then, if so desired, passed through a second impregnating bath wherein the noble metal of the Group VIII Periodic Table is deposited thereon. Alternatively, it is also contemplated that the noble metal and the rhenium may be co-impregnated in a single impregnation zone following which the impregnated solid support is calcined and thereafter subjected to a reducing step in which the impregnated support is continuously passed through a reducing zone at an elevated temperature while being subjected to a hydrogen flow. After passage through the reducing zone, the metal impregnated solid support is continuously withdrawn, and passed to a different impregnation zone wherein the composite is impregnated with cadmium utilizing a cadmium salt of the type previously discussed. The impregnation of the composite with cadmium is also effected at an elevated temperature in the presence of nitrogen for a period of time sufficient to deposit the desired amount of cadmium on the composite. The cadmium treated composite is then continuously withdrawn and passed to a second calcination zone where it is also calcined at an elevated temperature in the presence of nitrogen to form cadmium oxide. After passage through this latter calcination zone, the desired composite is continuously withdrawn and recovered.

The following examples are given for purposes of illustrating the efficiency of the novel reduction catalysts of the present invention to form unsaturated esters or alcohols in contradistinction to the type of esters which are prepared when utilizing conventional reducing catalysts.

EXAMPLE I

To illustrate the type of product which is obtained when using an ordinary reduction catalyst, such a catalyst was prepared by steam impregnating 125 grams of alumina with an aqueous solution containing 1.8 grams of ammonium perrhenate. Following the impregnation, the composite was calcined at a temperature of 500° C.

for a period of 1 hour in an air atmosphere and thereafter was reduced in a hydrogen atmosphere at a temperature of 500° C. for a period of 1 hour.

To run the reductive esterification reaction, 200 grams of oleic acid and 10 grams of the catalyst prepared according to the above paragraph were charged to a 1 liter stirred autoclave. The autoclave was sealed and flushed twice with hydrogen. Following this, hydrogen was charged to the autoclave until an initial operating pressure of 100 psig was reached. The autoclave was then heated to a temperature of about 300° C. and maintained thereat for a period of 4 hours, while stirring at a rate of 1100 rpm. During this reaction period, the autoclave was maintained at a pressure of about 1000 psig. At the end of the 4 hour period, heating was discontinued and the autoclave was allowed to return to room temperature. The excess pressure was discharged, the autoclave was opened, and the reaction product was removed from the autoclave.

The reaction product was dissolved in hot toluene and vacuum filtered through a solid absorbent to remove the catalyst. The filtrate was then stripped of toluene on a rotary evaporator and subjected to quantitative gas chromatographic analysis as well as quantitative IR and iodine value analysis. The analysis disclosed that there had been a 97% conversion of the oleic acid, but also a 90% saturation of the double bonds. The selectivity, which is defined as the percent of acid conversion divided by the percentage of double bond saturation, was 1.1.

EXAMPLE II

In this example, a catalyst was prepared by co-impregnating 50 grams of alumina with an aqueous solution containing 0.5 grams of rhenium as ammonium perrhenate and 0.05 grams of platinum as chloroplatinic acid. The steam impregnation was effected for a period of 4 hours. At the end of this time, the impregnated alumina was recovered, calcined at a temperature of 500° C. in an air atmosphere for a period of 1 hour, and thereafter reduced by treatment with hydrogen for an additional period of 1 hour while maintaining the temperature at 500° C.

In a manner similar to that set forth above, 200 grams of oleic acid and 10 grams of the catalyst were charged to a 1 liter stirred autoclave which was sealed and flushed with hydrogen. Hydrogen was pressed in until an initial pressure of 100 psig was reached and thereafter, the autoclave was heated to a temperature of 300° C. Upon reaching the desired temperature, the autoclave was further pressurized to 1000 psig and the autoclave was maintained at about 300° C. for a period of 4 hours, while stirring the reaction mixture at a speed of 1100 rpm. During the 4 hour reaction period, the pressure was maintained at about 1000 psig. Following the completion of the 4 hour period, heat was discontinued and, after the autoclave had returned to room temperature, the excess pressure was vented. The autoclave was opened and the reaction mixture which was recovered therefrom was treated in a manner similar to that set forth in Example I. Analysis of the reaction product by means of gas chromatography, iodine value and quantitative IR disclosed that there had been a 100% conversion of the oleic acid, but in addition, there had been a 100% saturation of the double bonds, the ester which was recovered comprising stearyl stearate. Therefore, the selectivity was 1.0.

EXAMPLE III

To illustrate the unexpected activity of the novel reduction catalyst of the present invention to catalyze a reducing reaction involving an unsaturated carboxylic acid with the attendant retention of unsaturation in the carbon atom chain, a catalyst was prepared by co-impregnating alumina in the form of spheres with an aqueous solution containing 1% rhenium to weight of alumina as ammonium perrhenate and 0.1% platinum to weight of alumina as chloroplatinic acid. The steam impregnation was allowed to proceed for a period of 4 hours, following which the impregnated alumina spheres were calcined at a temperature of about 500° C. for a period of 1 hour in an air atmosphere. Following the calcination, the impregnated spheres were then further heated at a temperature of 500° C. for an additional period of 1 hour in a hydrogen atmosphere to reduce the rhenium and platinum. Following this, the composite was then steam impregnated with a solution of cadmium acetate for a period of 4 hours. Thereafter, the cadmium impregnated deposit was calcined at a temperature of about 275° C. for a period of about 3 hours under a nitrogen atmosphere whereby cadmium oxide was formed on the composite.

The feed stock comprising 200 grams of oleic acid and 10 grams of the catalyst prepared according to the above paragraph was charged to a 1 liter stirred autoclave, which was then sealed and flushed twice with hydrogen. The autoclave was then pressured to 100 psig with hydrogen and heated to a temperature of 300° C. Upon reaching the desired operating temperature, the autoclave was further pressured to 1000 psig. The reaction was allowed to proceed for a period of 4 hours while maintaining the temperature at about 300° C. and the pressure of 1000 psig, the autoclave being stirred at a rate of 1100 rpm. At the end of the 4 hour period, heating was discontinued and, after the autoclave had returned to room temperature, the excess pressure was vented and the autoclave opened. The reaction mixture was dissolved in hot toluene and filtered through a solid absorbent to remove the catalyst. A portion of the product was stripped to obtain a white solid reaction product. Analysis of the product by iodine value disclosed that there had been only 44% double bond saturation, while quantitative gas chromatography showed a 98% conversion of the oleic acid, the selectivity, measured by the percent of acid conversion divided by the percentage of double bond saturation, being 2.2. The unsaturated product was found to contain both oleyl oleate and oleyl alcohol.

It is evident that a comparison of the results obtained in this example with those obtained in Examples I and II above discloses a selectivity to the desired unsaturated ester and alcohol at twice the selectivity obtained when using conventional reducing catalysts.

EXAMPLE IV

In this example, a novel reduction catalyst may be prepared by steam impregnating silica spheres with rhenium in the form of ammonium perrhenate and palladium in the form of chloropalladic acid for a period of time sufficient to deposit 1% rhenium and 0.1% palladium on the silica acid. The composite may be calcined and reduced at a temperature similar to that hereinbefore utilized. Thereafter, the resulting composite may be further impregnated with cadmium acetate and the cadmium impregnated composite may then be calcined to form cadmium oxide on the surface of the catalyst.

The thus produced catalyst may then be used in a reduction reaction involving crotonic acid utilizing conditions similar to those hereinbefore set forth to form crotonyl crotonate and crotonyl alcohol.

I claim as my invention:

1. A catalyst composite for the reduction of an unsaturated acid to an unsaturated alcohol or ester which comprises from about 1% to about 10% by weight of cadmium in the oxide form, and from about 0.5% to about 5% by weight of rhenium in an oxide form, both being composited upon a high surface area solid support.

2. The catalyst composite set forth in claim 1 in which said solid support is an alumina.

3. The catalyst composite set forth in claim 2 in which said alumina is gamma-alumina.

4. The catalyst composite set forth in claim 1 in which said solid support is silica.

5. The catalyst composite set forth in claim 1 in which said solid support is silica-alumina.

6. The catalyst composite of claim 1 further characterized in that said composite contains from about 0.01% to about 2.5% by weight of a Noble Metal of Group VIII of the Periodic Table.

7. The catalyst composite set forth in claim 6 in which said noble metal is platinum.

8. The catalyst composite set forth in claim 6 in which said noble metal is palladium.

* * * * *